United States Patent [19]

Isaacs et al.

[11] 4,043,890
[45] Aug. 23, 1977

[54] DEVICE FOR MEASURING THE TOTAL CONCENTRATION OF OXYGEN IN GASES

[75] Inventors: Hugh S. Isaacs, Shoreham; Anthony J. Romano, Kings Park, both of N.Y.

[73] Assignee: The United States of America as represented by the United States Energy Research and Development Administration, Washington, D.C.

[21] Appl. No.: 695,899

[22] Filed: June 14, 1976

[51] Int. Cl.² .................................... G01N 27/46
[52] U.S. Cl. ........................ 204/195 S; 204/1 T
[58] Field of Search .................. 204/1 S, 195 S

[56] References Cited

U.S. PATENT DOCUMENTS

| | | | |
|---|---|---|---|
| 3,791,953 | 2/1974 | Minushkin et al. | 204/195 S |
| 3,860,498 | 1/1975 | Jones | 204/195 S |
| 3,914,169 | 10/1975 | Horowitz | 204/195 S |
| 3,935,089 | 1/1976 | Togawa et al. | 204/195 S |
| 3,981,785 | 9/1976 | Sandler | 204/1 T |

*Primary Examiner*—T. Tung
*Attorney, Agent, or Firm*—Dean E. Carlson; Leonard Belkin

[57] ABSTRACT

This invention provides a CO equilibrium in a device for measuring the total concentration of oxygen impurities in a fluid stream. To this end, the CO equilibrium is produced in an electrochemical measuring cell by the interaction of a carbon element in the cell with the chemically combined and uncombined oxygen in the fluid stream at an elevated temperature.

3 Claims, 3 Drawing Figures

DEVICE FOR MEASURING THE TOTAL CONCENTRATION OF OXYGEN IN GASES

STATEMENT OF GOVERNMENT INTEREST

This invention was made in the course of, or under a contract with the United States Energy Research and Development Administration, and/or the National Regulatory Commission.

BACKGROUND OF THE INVENTION

In high temperature helium cooled nuclear reactors the presence of small amounts of gaseous impurities, such as oxygen or oxygen containing compounds, is an important factor in corrosion and mass transfer that affects the operating lifetime and safety of the reactor, as is well known in the art. Graphite and certain metals considered to be otherwise quite suitable for specific applications in a nuclear reactor, such as stainless steel and nickel alloys, for example, are readily reacted with, corroded by, or otherwise degraded in water, carbon dioxide or oxygen, even in very small amounts, such as a few parts per million (p.p.m) of the oxygen containing impurities.

While considerable precautions are generally taken to insure that the presence of oxygen containing impurities do not exceed the barest possible minimum, it is quite apparent that during normal operation of the reactor, regular tests for the presence of oxygen should be made to minimize the degradation of materials, e.g., by oxidation or carburization of metals, hydrolysis of fuel, and pitting of structural graphite components, and to minimize the movement of fission products, carbon transfer and the formation of particles in the primary reactor system. Furthermore, a sudden, though slight, increase in the oxygen impurity level present might be the first detectable indication of a failure or an otherwise undetected deviation from normal operation, and it would be exceedingly helpful if the increase were to be detected immediately so that corrective action could be taken before extensive damage occurs.

Among the various techniques and devices developed to measure the presence of oxygen containing impurities in fluid streams is the voltaic cell, such as the "Self-sealing Electro-chemical Oxygen Meter" described in U.S. Pat. No. 3,791,953, which issued on Feb. 12, 1974; U.S. Pat. No. 3,378,478, which issued on Apr. 16, 1968; and U.S. Pat. No. 3,711,394, which issued on Jan. 16, 1973.

In the aforementioned U.S. Pat. No. 3,711,394 an elongated tube in the form of a solid electrolyte is utilized. The long tube shape is dictated by the necessity for making a gas tight seal at low temperatures. Since elastomers are used, the seal is made at the top end where temperatures are low. However, the resulting cell assembly has had a temperature gradient from top-to bottom that has affected the performance of the cell assembly. Furthermore, in a reactor environment, the presence of radiation can lead to rapid deterioration of the elastomer seal.

The above described ceramic tubes have had the additional difficulty that they have been fabricated by slip-casting or isostatic pressing and then sintering. Thus, the dimensions of the finished tubes have been difficult to control accurately, and the slip-cast tubes in particular contained impurities that could deleteriously affect the electrochemical cell behavior. The isostatically pressed and sintered tubes have also been inordinately expensive and time consuming to manufacture, and they still have contained undesirable impurities.

To overcome many of the problems associated with the preparation and use of tubular shaped ceramic elements, special deformable metal seal rings have been used. Also, thin discs of electrolyte have been used to perform the function of the tubes, as described in U.S. Pat. No. 3,791,953 which is incorporated by reference herein. However, it was difficult or impossible with these cells to effectively and efficiently measure a substantially broad range of oxygen concentrations. This is because the electrolytes suffer from limitations due to the presence of electronic conduction at low oxygen concentrations, since the electronic conduction reduces the sensitivity of the measurements.

SUMMARY OF THE INVENTION

This invention overcomes the latter above-mentioned problems and disadvantages by providing a CO equilibrium in the described electro-chemical measuring cell for the detection of a broad range of concentrations of total oxygen impurities. For purposes of this invention the total oxygen impurities, comprise both chemically combined (i.e., compounds) and uncombined oxygen impurities in a fluid stream, such as a He gas stream for cooling nuclear reactors. For example, the impurities comprise $O_2$, $CO$, $CO_2$ and $H_2O$.

More particularly, in the preferred embodiment, the cell of this invention consists of a thin ceramic disc-shaped element having first and second oppositely facing surfaces of a solid electrolyte; respective oxygen containing reference and measurement gases in contact with the first and second oppositely facing surfaces of the electrolyte, carbon element means adjacent to the second surface for producing CO by a reaction between the carbon means and substantially all of the oxygen in the measurement gas in contact with the carbon means; housing means for supporting the disc-shaped element in contact with the measurement and reference gases on the opposite first and second sides of the electrolyte; and annular spring sealing means surrounding and sealing the disc-shaped element with the housing means for limiting the leakage of the measurement gas stream into the interior of the housing means thus to prevent the mixing of the measurement and the reference gases. A porous metallic coating on the reference gas side of the electrolyte is connected by electrically conducting means passing through and insulated from the side of the housing means to a meter also having a connection to the measurement gas through the housing means to complete the required circuit, while suitable source means supply the reference and measurement gases to the opposite sides of the electrolyte at suitable conditions respectively to maintain a small temperature gradient across the electrolyte, to convert all the oxygen in the measurement gas to CO to form a CO equilibrium on the measurement gas side of the electrolyte, and to maintain the electrically conducting means at ambient room temperature. With the proper selection of elements and steps, as described in more detail hereinafter, the desired measurement and CO equilibrium are achieved in a conventional electrochemical cell for increasing the sensitivity of the cell to the measurement of low concentrations of total oxygen impurities in the measurement gas stream.

OBJECTS OF THE INVENTION

It is an object of this invention, therefore, to provide means for measuring a broad range of concentrations of oxygen and oxygen containing species as impurities in a fluid stream.

It is another object to provide a carbon-monoxide equilibrium in an electro-chemical measuring cell for measuring the total oxygen in a high temperature He stream.

It is a still further object to measure the total oxygen and oxygen containing impurities in a gas stream in the presence of $H_2$.

The above and further novel features and objects of this invention will appear more fully from the following detailed description of one embodiment, when the same is read is connection with the accompanying drawings, and the novel features will be particularly pointed out in the appended claims.

BRIEF DESCRIPTION OF THE DRAWINGS

In the drawings, where like elements are referenced alike.

DESCRIPTION OF THE PREFERRED EMBODIMENT

This invention is useful for measuring a broad range of concentrations of total oxygen impurities in a fluid stream containing free oxygen, air, $O_2$, CO, $CO_2$ and/or $H_2O$. As such, this invention, is useful as a modification of the cell of U.S. Pat. No. 3,791,953, wherein the measured fluid stream is He gas containing oxygen rather than liquid sodium containing oxygen.

Figure 1:
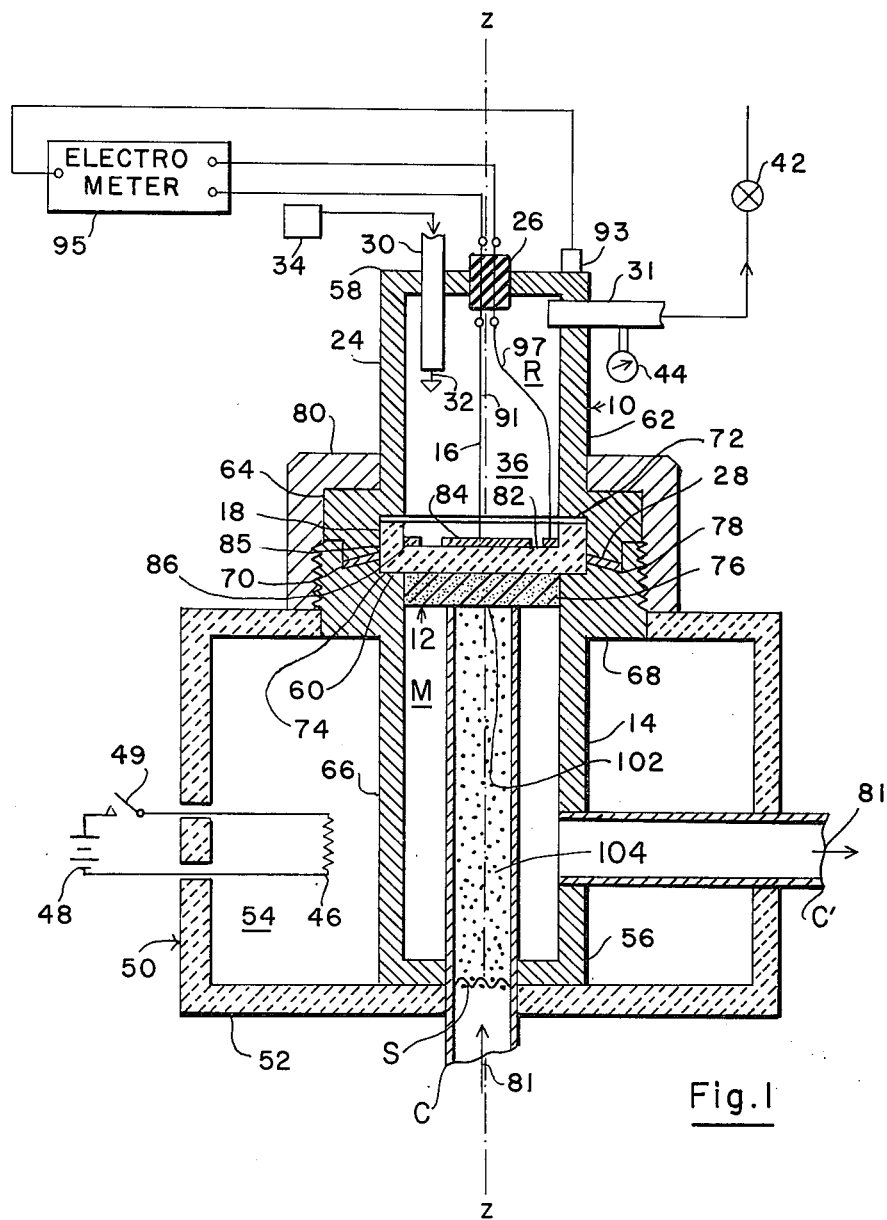
FIG. 1 is a partial cross-section of one embodiment of the apparatus of this invention.

Referring now to FIG. 1, electrochemical cell 10 consists of an assembly 12 having a measuring first electrode 14 and a reference second electrode 16, which are connected to the opposite sides of a disc of an electrolyte 18 in contact respectively with a reference gas R and a measurement gas M. A wide range of electrolytes and electrodes may be used. For example, the electrolyte 18 may advantageously be yttrium doped thorium oxide ceramic, and the electrodes 14 and 16 may be stainless steel. Also, the electrodes are supported by a housing means 24 having an electrical insulator 26 and annular metallic spring sealing means 28, such as stainless steel, forming a positive seal between the electrolyte 18 and the housing 24 to prevent the measurement and reference gases from mixing, e.g. by letting measurement gas enter into the upper portion of the housing.

Advantageously, the housing 24 has disposed in the sides thereof two longitudinally extending conduits 30 and 31 for receiving and transporting a reference oxygen containing gas stream 32 under pressure from a suitable source 34 so as to fill chamber 36 with the reference gas. By suitably adjusting the release of the gas stream 32 from chamber 36 through valve 42, the velocity of the gas in chamber 36 is selectively adjusted; likewise, the pressure in chamber 36 is selectively adjusted, as indicated by gage 44. The flow of gas stream 32 may be reversed, or alternately a sealed system may be employed, in which case the chamber 36 is alternately periodically purged. The gas stream 32 contains a uniform, constant, fixed amount of air, pure oxygen, or oxygen mixed with an inert gas, such as argon, or a fixed amount of metallic oxide, since the latter maintains a uniformly constant oxygen concentration in the measurement gas stream.

Figure 2:
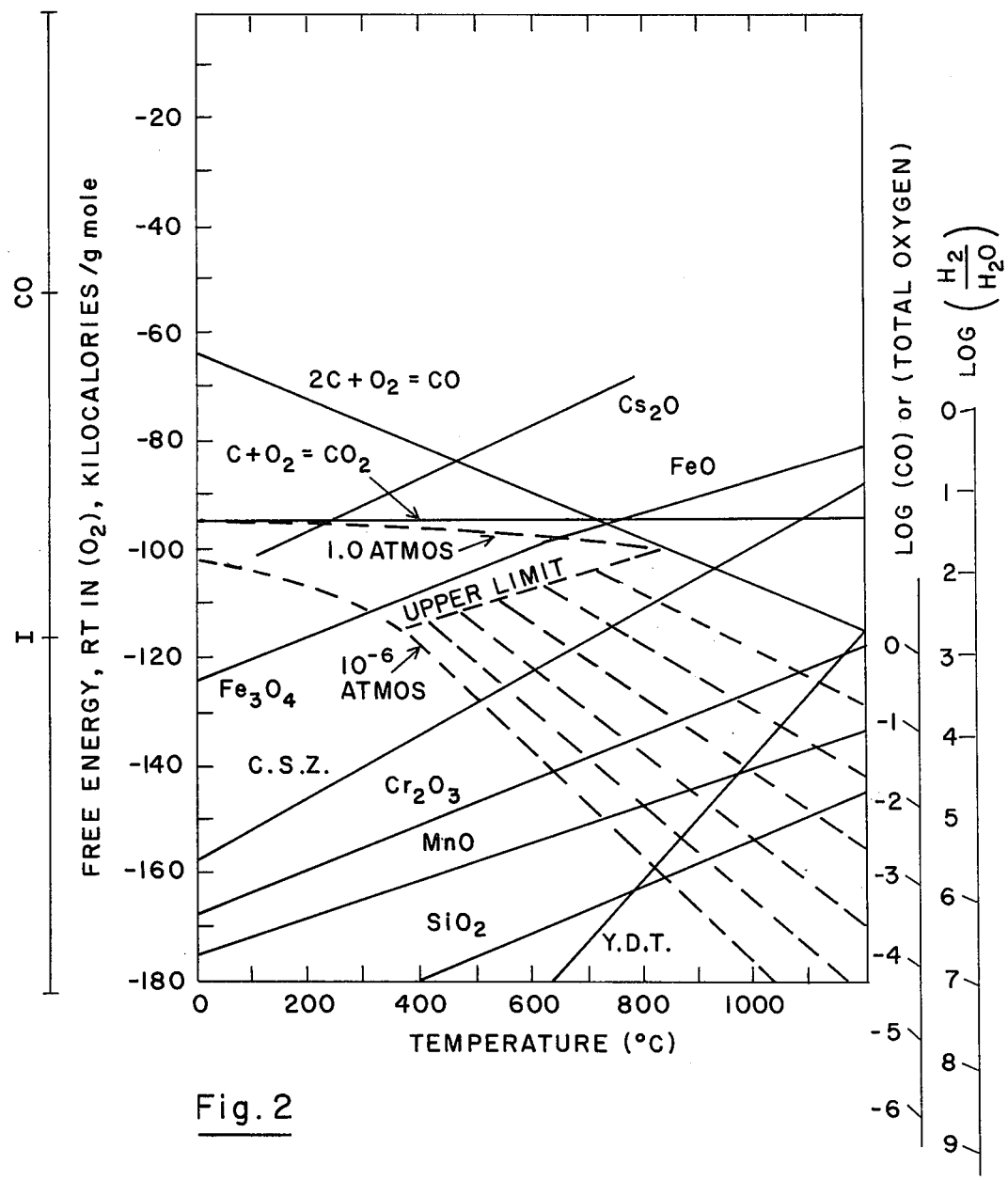
FIG. 2 is a graphic illustration of the free energy of formation of some oxides and the equilibrium oxygen potentials for various pressures of water reacted with carbon as a function of temperature, as described in BNL Report 19763, published June 30, 1975, in NSA 35522.

Advantageously, a heating element 46 having a power source 48 and control 49 are provided for a furnace 50 having walls 52 enclosing and insulating the space 54 around the bottom end 56 of the cell 10 to heat the measurement gas on one side of the electrolyte at the bottom of the cell. Meanwhile, the top end 58 of the cell, which contains the reference gas on the other side of the electrolyte, is at or near ambient temperature, and there is a small temperature gradient from the top to the bottom of the electrolyte 18, since the electrolyte is provided by a thin ceramic plate or disc 60. The desired temperatures provide oxygen potentials at which electronic conduction reaches 1% of the total conduction in the electrolyte, as shown in FIG. 2.

The thin ceramic circular plate or disc 60 of the electrolyte 18 is mounted as illustrated within housing 24, which has an upper closure 62 with a flange 64 and a lower cylindrical housing 66 with a flange 68. By assembling the housing 24, as shown, the latter forms an annular groove 70 with upper and lower shoulders 72 and 74. A tight-fitting, flat, annular, metallic spring 76 surrounds disc 60, and is compressed as shown, so that at the most only small spaces 78 are formed between the spring and the groove 70 in the upper and lower shoulders when the housing 24 is assembled. Flanges 64 and 68 may be locked together by a threaded clamp 80 or bolts (not shown). Due to the tight fit and sealing principle of spring 76, which may react with oxygen to form a tighter seal, no leakage of the measurement gas stream 81 past the spring occurs. Thus, there is no mixing of the measurement gas and the reference gas from one side of the electrolyte to the other.

In order to insure proper contact between the bottom side of the disc 60, i.e., on one side of the electrolyte, and the measurement gas stream 81 whose oxygen content is to be measured, a conduit C is provided to deliver the gas stream up to the bottom surface of disc 60 while the lower housing 66 is provided with a conduit extension C' to carry away the measurement gas stream, as shown by the arrows. A pump not shown in conduit C may be provided to obtain the desired circulation, while, if desired, the flow may be reversed. Assembly 12 is installed in the system so that the gas stream 81 to be measured flows into the lower cylindrical housing 66 past or along the flat first surface the electrolyte 18 of disc 60 and exits at the bottom of the housing 66 without reacting with the disc.

On the other side, a flat second surface of disc 60 is provided with a central narrow section 82 on which is deposited a porous coating or layer 84 of any metal in which oxygen will dissolve but with which it will not react, and an annular thickened section 85 on which is deposited another separate metal layer 86 of a similar metal spaced as illustrated. Layer 84 may occupy the central portion of disc 60, as illustrated, and may be surrounded by a separate annular layer 86, neither layer contacting each other or the metal housing 24.

The ceramic electrolyte 18 employed for disc 60 is a solid metallic oxide that has a crystal structure containing oxygen ion vacancies. U.S. Pat. No. 3,481,855, which is incorporated by reference herein, identifies suitable electrolytes for this invention.

An electrical connection wire 91, preferably of stainless steel, is spot welded or otherwise electrically connected to coating layer 84 and extends through the top end of housing 24 passing through a hermetically sealed electrical insulator 26, where it may be joined to ordinary copper conductors. The galvanic electrochemical cell, of which assembly 12 is a part, is completed by contact 93 making contact with the measurement gas stream 81 through stainless steel housing 24 at approximately the same temperature as wire 91. A differential voltmeter 95 in the circuit measures the EMF generated and provides an auxiliary or guard voltage, equal to the EMF generated, to ring layer 86, through a suitable conductor 97. If the annular metal layer (guard ring) is not used the auxiliary guard voltage is not required.

Should the second surface of the electrolyte 18, i.e., disc 60, be adjacent and in uniform contact with the first side of a porous carbon block 102, as described in more detail hereinafter, and should the oxygen in the incoming gas stream 81 be heated and transported slowly through the block after flowing through small diameter carbon particles 104 to form a carbon dioxide equilibrium therewith adjacent the second side of the block 102, as shown in FIG. 1, the potential across the electrolyte 18 can be used to monitor any concentrations of total oxygen in the measurement He gas stream 81, whether it contains CO, $CO_2$, $H_2$, oxygen, air or water. To this end, the large surface area of the carbon particles, the low velocity of the gas stream, and the elevated temperature thereof, causes substantially all the oxygen in the measurement gas stream to be converted to CO in the form of an equilibrium that is directly proportional to the total combined and uncombined oxygen in the gas stream. Thus, the oxygen potential in the cell is readily related to the total CO concentration, which in turn gives the total oxygen concentration in the gas stream.

In actual practice, the system has been shown to be virtually independent of hydrogen concentrations above an initial partial pressure of 1.0 atmosphere (20,000 Vpm $H_2$) with an error of less than 50% in oxygen concentrations at any levels, even below one Vpm total oxygen.

The required carbon means is supplied by a porous graphite block and finely divided, graphite particles piled up on a screen S in inlet tube C whose cross-section is symmetrical around an axis of rotation Z—Z down the middle of the longitudinally extending, tubular-shaped housing. These carbon particles and this carbon block are formed by conventional means.

In the particular embodiment described, either gold or platinum may be used for layers 84 and 86, as described in U.S. Pat. No. 3,791,953, which is incorporated by reference herein, since such layers do not react with carbon in an oxygen containing ambient.

In operation, the base for the coatings is advantageously a ceramic electrolyte 18, that performs a function analgous to the function of the "disc 12" of the cited Minuskin et al U.S. Pat. No. 3,791,953. To this end, the ceramic of electrolyte 18 is solid material that has a crystalline structure containing oxygen ion vacancies, such that at the high temperatures produced in chamber 54 at the bottom 56 of the cell by heating element 46, the ceramic electrolyte 18 conducts electricity predominantly by the migration or transfer of oxygen ions through the crystalline structure of the electrolyte. Materials of this type are known in the art and are more particularly identified in the aforementioned U.S. Pat. No. 3,481,855. In the particular embodiment described herein, this ceramic electrolyte 18 is $ThO_2$ with a minor amount (less than 50%) of $Y_2O_3$, for example 15 w/o $Y_2O_3$ or 7.5 w/o $Y_2O_3$. This is because calcia stabilized zirconia may be used only at the low temperature of ~ 500° C, which is below the temperature required for producing the desired CO equilibrium.

The galvanic, electro-chemical cell 10, of which assembly 12 is a part, measures the voltage produced by the contact 93 that makes electrical connection with the gas stream 81 through the stainless steel of housing 24, as a measure of the oxygen in the gas stream 81. To this end, the volt meter 95 is placed in the described circuit with wire 91 to measure the EMF generated.

The conduit 30 passing through the top of the housing 24 supplies the oxygen containing reference gas stream 32 within the assembly 12, while conduit 31 carries away the exhausting gas stream 81. The oxygen containing impurities in the measurement fluid stream 81 may be free oxygen or a compound, i.e., chemically uncombined or combined oxygen, such as CO, $CO_2$ or $H_2O$. Likewise, the reference gas stream may contain He or other inert gases.

From the above, it will be understood that this invention is useful in determining the total oxygen in a gas coolant stream for a nuclear reactor. To this end, in a helium gas which has mixtures of oxygen containing species, the oxygen activity of the gas will depend on the species concentrations and their ratios as well as the presence of hydrogen. When this gas is equilibrated with carbon the oxygen bearing species are converted to CO and the oxygen activity can be defined in terms of concentration of CO and is not complicated by the presence of hydrogen up to very high levels approaching 1 atmosphere. Thus, the CO equilibrium of this invention acts as an integrator for the total oxygen, both combined and uncombined, in the gas stream, even when the gas stream contains several oxygen containing species, such as $O_2$, CO, $CO_2$ and $H_2O$, since each species is converted into CO.

The following are examples of the apparatus of FIG. 1:

EXAMPLE I

In the arrangement described for the preferred embodiment, the measurement gas stream contains $H_2$, He and $O_2$ at a velocity of 1–50cc/min, and the reference gas stream is air, which circulates at between 1cc/min and 500cc/min. The porous first layer 84 would have a typical thickness of about 0.1 micron while disc 60 in its central section would have a thickness of about 1/32 to ⅛ inch. The electrolyte material for the disc 60 would be $ThO_2$ — 15 w/o $Y_2O_3$ and the temperature of the gas to be measured is about 650° C or higher to make sure that all the oxygen in the gas to be measured is converted to CO. Without the CO equilibrium the cell sensitivity is reduced at low concentrations of oxygen in the measurement gas stream. Thus, a porous carbon block and graphite particles increase the sensitivity, and the removal of the same decreases the sensitivity at low oxygen concentrations in the measurement gas stream. The CO concentration is directly proportional to the total oxygen concentration in the measurement stream, and the relation between the oxygen potential and temperature are linear within the limits shown in the "upper limit" in FIG. 2. The measurement is independent of the hydrogen and He concentrations.

EXAMPLE II

The steps of Example I are repeated using a porous carbon block 102 on top of graphite particles having an average particle cross-section of 1mm across filled in a stainless steel tube and held therein on a stainless steel screen. All the gas to be measured is transported through the graphite particles and carbon block at 650° C at 1cc/min, such that when the oxygen containing measurement gas stream 81 is introduced into the first electrode 14, the oxygen in the gas stream produces an equilibrium of CO in the chamber. This enhances the sensitivity of the cell in measuring the total oxygen, since the voltmeter is more sensitive and responsive over a wider range of total oxygen concentrations. To this end, this CO equilibrium system of this invention improves the measurement of the total oxygen concentration in the gas stream to be measured in the described cell over the range of total oxygen concentration from one atmosphere down to less than one part per million, as discussed in Brookhaven Laboratory Report 19763, which is incorporated by reference herein (see pp 2-1 to 2-5).

EXAMPLE III

The steps of Example II are repeated with 10 grams of graphite particles for gas streams to be measured containing CO, $CO_2$, $H_2O$, $O_2$ (pure) and/or $O_2$ mixed with an inert gas, such as argon or helium respectively. It appears that the electrolytes used in the cited U.S. Pat. No. 3,791,953 do not react with oxygen on either side of the disc, and that such is required. It also appears that the same amount of graphite particles with reduced surface area, e.g., those that are larger than 10 millimeters across, can reduce the reaction rate. Thus, either a CO equilibrium is not formed, or the gas velocity has to be decreased inordinately even at high temperatures above 850° C. It appears further that the measurement stream has to be at 650° C or above to insure the conversion of all the measurement oxygen to CO. For example, at a temperature of below 600° C, $CO_2$ predominates, and the oxygen potential approaches that for $CO_2$, as expected from FIG. 2.

EXAMPLE IV

The steps of Example II are repeated using a reference gas stream containing air, pure oxygen, and/or oxygen mixed with an inert gas or a mix of metallic oxide and its metal to insure that the reference gas stream contains a constant oxygen concentration.

This invention has the advantage of providing an effective, sensitive and accurate measure of the total oxygen concentration in a He gas stream by producing a CO equilibrium therein in a conventional electro-chemical cell apparatus for measuring oxygen in a gas stream. To this end, this invention has the advantage of decreasing the limitation suffered by conventional electrolytes due to the presence of electronic conduction at low oxygen concentrations. Thus, this invention negates the effect of this electronic conduction in reducing the sensitivity of the measurements of conventional electro-chemical cells for measuring total oxygen concentrations in He gas stream.

What is claimed is:

1. An electrode assembly for use in a cell for the detection of the total oxygen in a gas stream whose oxygen content is to be measured comprising:
   a. a thin disc-shaped solid-electrolyte element having oppositely facing first and second surfaces;
   b. a porous coating layer of metal in which oxygen will dissolve but not react covering at least a portion of the first surface of the disc-shaped element;
   c. carbon means adjacent the second surface for producing CO by a reaction between the carbon means and oxygen;
   d. housing means for supporting the disc-shaped element for partial exposure to the gas stream whose oxygen content is to be measured, such that the latter would be in contact with the second surface of said disc-shaped element;
   e. annular spring sealing means surrounding and sealing the disc-shaped element to limit leakage of the measurement gas stream from the second side of the disc-shaped element into the interior of said housing means for preventing the measurement gas and a reference gas from mixing on the first side of the disc-shaped element;
   f. contact means of electrically conducting material in contact with said porous coating layer of metal and extending through and out of the interior of said housing means;
   g. means supplying an oxygen containing reference gas into said housing means and in contact with said porous coating layer of metal;
   h. means having a heater for supplying said gas stream whose oxygen content is to be measured to said second surface and circulating it slowly through the carbon means adjacent thereto for converting all the oxygen contained in the measurement gas stream to CO at an elevated temperature for producing said CO in an equilibrium with the total amount of oxygen in the gas stream; and
   i. means connected to the contact means and the second surface of the solid electrolyte element for measuring the electrical potential difference across the electrolyte as a measure of the oxygen in the gas stream to be measured;
   j. the CO equilibrium directly corresponding substantially with the concentration of the total oxygen in the gas stream on the other side of the electrolyte for reducing the electronic conduction of the electrolyte at low oxygen concentrations, thus to increase the sensitivity of the electrical potential difference across the electrolyte as a measure of the total oxygen in the gas stream whose oxygen content is to be measured.

2. The assembly of claim 1 in which the coating of metal is selected from the group consisting of platinum and gold, and the carbon means comprises a carbon block and graphite particles having an average width only up to 1 mm.

3. The assembly of claim 2 having means to mantain the gas stream to be measured in continuous contact with the second surface of said disc-shaped element, and means for heating the measurement gas stream to at least 650° C while in contact with the second surface and while maintaining the contact means of the electrically conducting material extending out of the housing at a lower ambient room temperature.

* * * * *